(12) United States Patent
Crank (10) Patent No.: US 8,852,084 B2
(45) Date of Patent: Oct. 7, 2014

(54) ORIENTATION ADAPTER FOR INJECTION TUBE IN FLEXIBLE ENDOSCOPE

(75) Inventor: Justin M. Crank, Maple Grove, MN (US)

(73) Assignee: AMS Research Corporation, Minnetonka, MN (US)

( * ) Notice: Subject to any disclaimer, the term of this patent is extended or adjusted under 35 U.S.C. 154(b) by 215 days.

(21) Appl. No.: 13/168,565

(22) Filed: Jun. 24, 2011

(65) Prior Publication Data

US 2011/0313248 A1 Dec. 22, 2011

Related U.S. Application Data

(62) Division of application No. 11/937,728, filed on Nov. 9, 2007, now Pat. No. 7,993,264.

(60) Provisional application No. 60/865,010, filed on Nov. 9, 2006.

(51) Int. Cl.
| | |
|---|---|
| *A61B 1/12* | (2006.01) |
| *A61B 1/307* | (2006.01) |
| *A61B 1/018* | (2006.01) |
| *A61B 1/00* | (2006.01) |
| *A61B 1/04* | (2006.01) |

(52) U.S. Cl.
CPC ............. *A61B 1/018* (2013.01); *A61B 1/00091* (2013.01); *A61B 1/307* (2013.01); *A61B 1/00131* (2013.01); *A61B 1/00101* (2013.01)
USPC ............................. 600/156; 600/127; 600/129

(58) Field of Classification Search
USPC ......... 600/104, 123–125, 127, 133, 154–158; 604/166.01
See application file for complete search history.

(56) References Cited

U.S. PATENT DOCUMENTS

| | | | |
|---|---|---|---|
| 4,093,108 A | 6/1978 | Hein et al. | |
| 4,130,119 A | 12/1978 | Sessions et al. | |
| 4,742,817 A | 5/1988 | Kawashima et al. | |
| 4,946,442 A | 8/1990 | Sanagi | |
| 5,007,897 A | 4/1991 | Kalb | |
| 5,116,313 A | 5/1992 | McGregor | |
| 5,261,889 A | 11/1993 | Laine et al. | |
| 5,336,178 A | 8/1994 | Kaplan | |
| 5,630,795 A * | 5/1997 | Kuramoto et al. | 604/30 |
| 5,693,016 A | 12/1997 | Gumaste et al. | |
| 5,718,709 A * | 2/1998 | Considine et al. | 606/115 |
| 5,840,062 A | 11/1998 | Gumaste et al. | |
| 6,203,533 B1 | 3/2001 | Ouchi | |
| 6,210,378 B1 | 4/2001 | Ouchi | |
| 6,238,336 B1 | 5/2001 | Ouchi | |

(Continued)

FOREIGN PATENT DOCUMENTS

| | | |
|---|---|---|
| WO | WO9616606 A1 | 6/1996 |
| WO | WO9736625 A1 | 10/1997 |

(Continued)

*Primary Examiner* — Alireza Nia (74) *Attorney, Agent, or Firm* — Kagan Binder, PLLC (57) ABSTRACT

An endoscope adapter ring for a needleless fluid delivery system for delivering therapeutic fluids to treatment sites within a patient. The needless fluid delivery system can include an automated injector source and a needleless access device. The access device can include a delivery scope and a treatment specific applicator. The adapter ring is operably attached to the endoscope to keep the injector lumen in a known orientation for the use of a side injector.

16 Claims, 5 Drawing Sheets

(56) References Cited

U.S. PATENT DOCUMENTS

| | | |
|---|---|---|
| 6,280,413 B1 | 8/2001 | Clark et al. |
| 6,400,980 B1 | 6/2002 | Lemelson |
| 6,537,205 B1 | 3/2003 | Smith |
| 6,547,767 B1 | 4/2003 | Moein |
| 6,621,005 B1 * | 9/2003 | Lovec et al. ............... 174/74 R |
| 6,641,553 B1 | 11/2003 | Chee et al. |
| 6,905,475 B2 | 6/2005 | Hauschild et al. |
| 7,316,679 B2 * | 1/2008 | Bierman ..................... 604/535 |
| 7,749,156 B2 | 7/2010 | Ouchi |
| 2003/0163111 A1 | 8/2003 | Daellenbach |
| 2004/0030320 A1 | 2/2004 | Chee et al. |
| 2004/0162528 A1 | 8/2004 | Horvath et al. |
| 2005/0192530 A1 | 9/2005 | Castellano |
| 2005/0228225 A1 | 10/2005 | Hauschild et al. |
| 2006/0129125 A1 | 6/2006 | Copa et al. |
| 2007/0167921 A1 | 7/2007 | Burren et al. |
| 2007/0225554 A1 | 9/2007 | Maseda et al. |
| 2008/0114203 A1 | 5/2008 | Crank |
| 2008/0119784 A1 | 5/2008 | Roychowdhury |
| 2008/0119823 A1 | 5/2008 | Crank |
| 2009/0124974 A1 | 5/2009 | Crank et al. |
| 2009/0312696 A1 | 12/2009 | Copa et al. |
| 2011/0015614 A1 | 1/2011 | Rykhus, Jr. et al. |
| 2011/0046600 A1 | 2/2011 | Crank |

FOREIGN PATENT DOCUMENTS

| | | |
|---|---|---|
| WO | WO0040279 A1 | 7/2000 |
| WO | WO0066199 A1 | 11/2000 |
| WO | WO0136029 A1 | 5/2001 |
| WO | WO0207812 A2 | 1/2002 |
| WO | WO2004071612 A2 | 8/2004 |
| WO | WO2005094921 A1 | 10/2005 |
| WO | WO2006057604 A1 | 6/2006 |
| WO | WO2006063180 A2 | 6/2006 |
| WO | WO2006076699 A1 | 7/2006 |
| WO | WO2006084821 A2 | 8/2006 |
| WO | WO2006086719 A2 | 8/2006 |
| WO | WO2007038591 A2 | 4/2007 |
| WO | WO2007079152 A2 | 7/2007 |
| WO | WO2010065126 A2 | 6/2010 |
| WO | WO2010065127 A2 | 6/2010 |
| WO | WO2010065133 A2 | 6/2010 |
| WO | WO2010074705 A2 | 7/2010 |
| WO | WO2010077271 A2 | 7/2010 |
| WO | WO2011011423 A1 | 1/2011 |

* cited by examiner

ORIENTATION ADAPTER FOR INJECTION TUBE IN FLEXIBLE ENDOSCOPE

RELATED APPLICATIONS

This application is a division of application Ser. No. 11/937,728 filed Nov. 9, 2007, which claims the benefit of U.S. Provisional Application No. 60/865,010, filed Nov. 9, 2006, each which is hereby fully incorporated herein by reference.

FIELD OF THE INVENTION

The present invention relates generally to the delivery of therapeutic fluids. More specifically, the present invention relates to an adapter for an endoscope so that an injection lumen can be used to provide side firing injections to an internal treatment site.

BACKGROUND OF THE INVENTION

A wide variety of medical treatments are at least partially performed through the delivery and introduction of therapeutic compositions to a treatment location. Lower urinary tract health is an increasingly important health issue, e.g., based on an aging population. Prostate disease, for example, is a significant health risk for males. Diseases of the prostate include prostatitis, benign prostatic hyperplasia (BPH, also known as benign prostatic hypertrophy), and prostatic carcinoma.

Prostatitis is an inflammation of the prostate gland. Prostatitis is caused by bacterial infection in many instances, in which case treatment generally includes antimicrobial medication. Noninfectious forms of prostatitis are treated by other means such as administration of an alpha-1-adrenoreceptor antagonist drug to relax the muscle tissue in the prostate and reduce the difficulty in urination. Benign prostatic hypertrophy (BPH) is a very common disorder affecting an estimated 12 million men in the United States alone. BPH is a non-cancerous condition characterized by enlargement of the prostate, obstruction of the urethra, and gradual loss of bladder function. BPH may be treated with a number of therapeutic modalities including surgical and medical methods, depending on severity of symptoms. Treatments range from "watchful waiting" for men with mild symptoms, to medications, to surgical procedures.

Surgical methods used to relieve the symptoms of BPH include methods of promoting necrosis of tissue that blocks the urethra. Hyperthermic methods, for example, use the application of heat to "cook" tissue and kill the cells. The necrosed tissue is gradually absorbed by the body. Several methods of applying heat or causing necrosis have been demonstrated, including direct heat (transurethral needle ablation, or TUNA), microwave (transurethral microwave treatment, or TUMT), ultrasound (high-intensity focused ultrasound, or HIFU), electrical vaporization (transurethral electrical vaporization of the prostate, or TUEVP) and laser ablation (visual laser ablation of the prostate, or VLAP), among others.

Chemical ablation (chemoablation) techniques for promoting prostate tissue necrosis have also been considered. In one chemical ablation technique, absolute ethanol is injected transurethrally into the prostate tissue. This technique is known as transurethral ethanol ablation of the prostate (TEAP). The injected ethanol causes cells of the prostate to burst, killing the cells. The prostate shrinks as the necrosed cells are absorbed.

To inject the prostate, a transuretheral flexible endoscopic probe is typically directed to the area of interest. Because a flexible endoscope is rotated inside bends the injection tube will tend to uncontrollably rotate inside the channel of the endoscope because it does not have equal bending stiffness in all degrees of movement. Moreover, the articulating section of the flexible endoscope can typically only bend on one direction making compound bends impossible. This is a problem in the anatomy around the prostate. Therefore there is a need to fix the injection tube in a preselected orientation so as to enable an injection in the desired direction.

SUMMARY OF THE INVENTION

The invention relates to needleless devices useful for injecting fluid to tissue of the lower urinary tract such as the prostate. The devices inject a therapeutic fluid or "injectate" at high-pressure using an orifice at the end of an elongate shaft inserted into the urethra. To treat the prostate, the injectate fluid passes through the urethra and disperses in the prostate as a cloud of particles. The needleless systems can overcome undesired or disadvantageous features of systems.

In a first embodiment, the needleless injector device as described can be used with various delivery methods such as methods that allow for direct vision of an injection wherein an internal location of an injection orifice is determined visually. Direct vision methods involve the use of an optical feature to view an injection site directly, such as by use of an endoscope or optical fiber that is included in an injector device, e.g., as a component of the shaft.

Endoscopes used for such surgery have outer tubes which are placed into the patient's urethra. Inner pathways within the endoscope provide a number of passages for guiding the treatment devices as well as the optical visualization system. The surgical or treatment instrument in this embodiment is a needleless injector device. The needleless injector device includes a body at a proximal end; a flexible shaft extending from the body to a distal end of the shaft; at least one injection orifice at the distal end of the shaft in fluid communication with a fluid chamber at the proximal end; and a pressure source in communication with the fluid chamber. The main body of the endoscope comprises actuators driving the surgical instrument, for instance to reciprocate it axially. As a rule, the endoscope also comprises fittings for flushing water with which the area of surgery is flushed to achieve better viewing.

As regards the present invention, the injector lumen is held in a known orientation within the endoscope by the disposition of an adapter within the working channel of the endoscope. This adapter is shaped such that it mates with a non-circular injection tube so as to prevent the rotation of the injection tube within the working channel. This eliminates the uncontrolled aspect of the injector lumen moving within the channel from rotation of the endoscope so that the operator does not know where the injector orifice is directed.

For example, the injection tube could have a rectangular cross section which would mate with the working opening of the adapter, thus preventing rotation. The adapter has at least one more opening to allow for irrigation fluid to flow through the working channel of the scope. The openings created by the adapter do not have to be defined by a cross-section. The adapter can define openings for the injection tube and fluid passage in conjunction with the surface of the working channel scope. This increases the area for the openings for further uses, such as the addition of additional tools.

The above summary of the various representative embodiments of the invention is not intended to describe each illustrated embodiment or every implementation of the invention. Rather, the embodiments are chosen and described so that others skilled in the art may appreciate and understand the principles and practices of the invention. The figures in the detailed description that follows more particularly exemplify these embodiments.

BRIEF DESCRIPTION OF THE DRAWINGS

The invention may be more completely understood in consideration of the following detailed description of various embodiments of the invention in connection with the accompanying drawings, in which.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives.

DETAILED DESCRIPTION OF THE DRAWINGS

In the following detailed description of the present invention, numerous specific details are set forth in order to provide a thorough understanding of the present invention. However, it will be obvious to one skilled in the art that the present invention may be practiced without these specific details. In other instances, well-known methods, procedures, and components have not been described in detail so as to not unnecessarily obscure aspects of the present invention.

Due to geometry, plastic deformation and material properties, the injection shaft containing an injection lumen may not match the orientation of a flexible cystoscope or endoscope in which it is housed or sheathed. For this application, applicant uses cystoscope and endoscope interchangeably as endoscope is a more general term for a tubular instrument fitted with a light and visualization system, while cystoscope typically refers to the device of this type used to examine the urethra.

For example, placement of the endoscope within the area of the prostate may require a number of bending actions of the endoscope which may result in the injector lumen bending or moving at a different rate or direction. Where the injection lumen was aligned with the visual field of the endoscope at the beginning of the procedure may no longer be the case by the time the endoscope is positioned relative to the prostate. This can be especially problematic if the injection is to be lateral as opposed to out the distal end of the injector lumen. The orientation needs to remain constant so that the injection always takes place with respect to the visual field and in the same spot.

The orientation matching may be accomplished in a first embodiment by placing an adapter ring that does not allow rotation of the injection lumen with respect to the flexible cystoscope. The adapter may optionally allow the injection lumen to advance or retract axially with respect to the cystoscope. The adapter ring may be attached to the cystoscope and/or the injection shaft. The attachment to either can be a press fit, a snap fit, a bond, a magnetic connection or other suitable methods.

Figure 1:
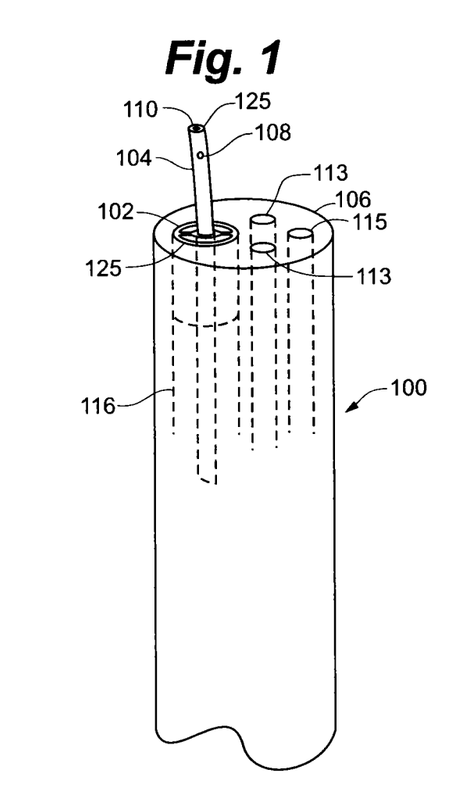
FIG. 1 is a perspective view of an embodiment of an endoscope with a needleless fluid delivery system for delivering a therapeutic fluid to a treatment location according to the present invention.

FIG. 1 illustrates a portion of the cystoscope 100 in perspective view so as to show the interaction of the adapter ring 102 and injection shaft 104. The injection shaft 104 extends beyond the distal end 106 of the cystoscope 100. As illustrated in FIG. 1, the injection shaft 104 includes a side orifice 108 and a distal end orifice 110. The present invention is most applicable to the utilization of the side orifice 108.

Figure 1A:
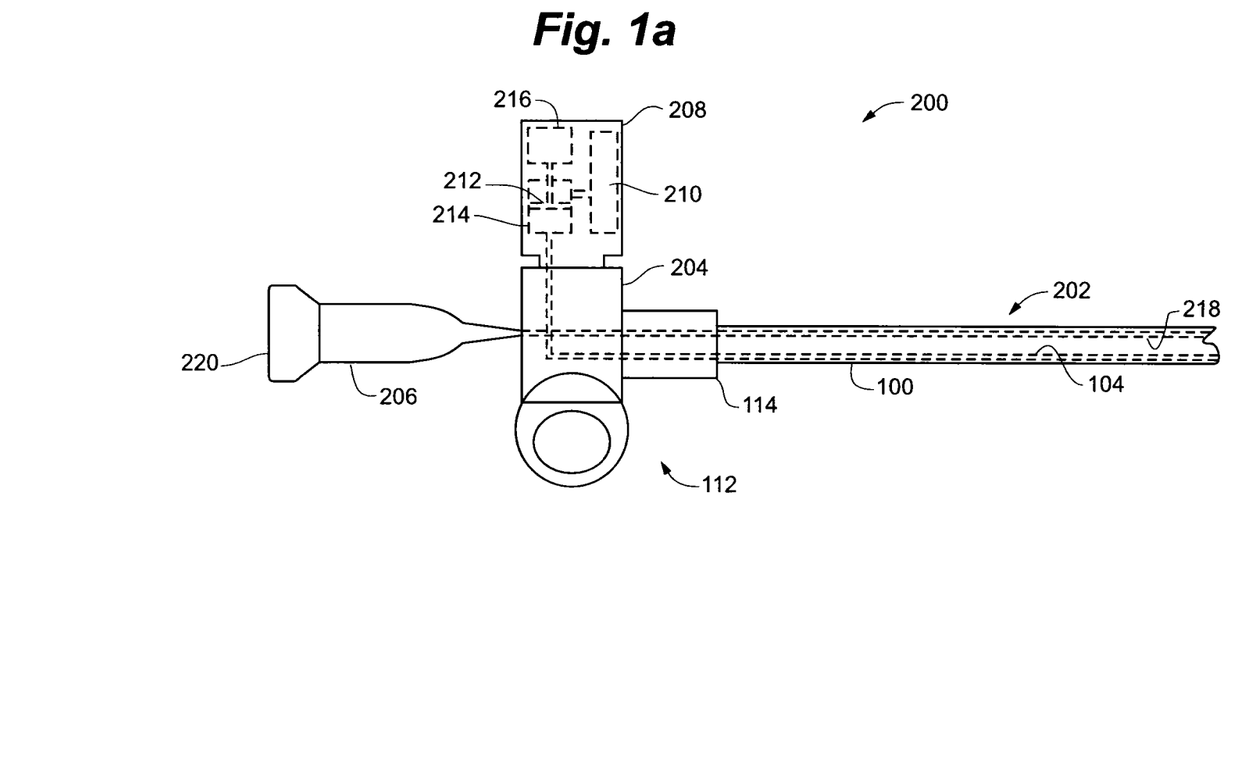
FIG. 1a is a side, partially hidden view of an embodiment of a needleless fluid injector device.

Cystoscope 100 includes a proximal portion 112 that remains external to the patient during use as shown in FIG. 1a. A proximal end 114 generally includes features that are not required to be internal during the treatment but instead are utilized to pressurize and deliver fluid through the injection shaft 104. For example, a needleless fluid delivery system is generally operably connected to the injection shaft 104. The needleless fluid delivery system includes features for providing injectate fluid and pressure to inject the fluid through the selected orifice. The needleless fluid delivery system generally includes a power supply or input for pressurizing the fluid and the associated valving and tubing. The pressure source can be pneumatic, hydraulic, mechanical (e.g., a spring), electric, or a pressurized gas cartridge. The proximal portion 112 can further provide optical features for viewing the treatment site including at least one lighting fiber optic 113 and one viewing fiber optic 115.

Referring to FIG. 1a, one representative embodiment of the needleless fluid delivery system can comprise an injector device 200 as described and illustrated within U.S. Patent Publication 2006/0129125A1, which is assigned to AMS Research Corporation of Minnetonka, MN and his hereby incorporated by reference in its entirety. Injector device 200 can be integral to the cytoscope 100 or injection shaft 104 and can include a main body 204, viewing scope 206 and power source 208. Main body 204 generally allows for connection of the injection shaft 104 to the power source 208. Power source 208 includes features for providing injectate fluid and pressure to inject the fluid, e.g., a permanent or removable supply of injectate fluid in fixed-volume reservoir 210; a pressurizing mechanism (e.g., a plunger, bellows, syringe, etc.) 212 within a variable-volume chamber 214 and a pressure source 216 for supplying pressure to pressurizing mechanism 214, which may be pneumatic, hydraulic, mechanical (e.g., a spring), electric, pressurized gas such as a carbon dioxide cartridge, an external source of pressurized gas or fluid, etc. Also included in power source 208 are mechanisms such as associated valving and tubing so as to allow fixed-volume reservoir 210, pressurizing mechanism 212 and pressure source 216 to work together to pressurize a fluid for injection through injection shaft 104. Viewing scope 206 can include a scope shaft 218 and eye-piece 220. Main body 204 generally fluidly interconnects the power source 208 with the injection shaft 104 to deliver pressurized fluid injectate to distal end 106 of the cytoscope 100.

Figure 1B:
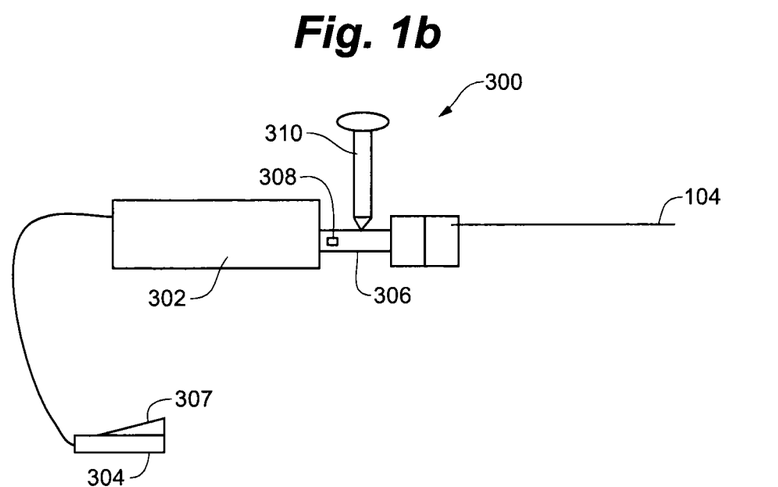
FIG. 1b is a schematic illustration of an embodiment of a needleless fluid injector device.

Referring to FIG. 1b, another representative embodiment of the needleless fluid delivery system can comprise an injector device 300 including an automated injector 302 having a user interface 304 and a connector member 306 for attaching to injection shaft 104. Connector member 306 can include a surface opening 308 and a therapeutic fluid supply 310. User interface 306 can comprise an input means for selectively delivering a pressurized fluid through the connector member 308. Representative input means can include foot pedal 307, switches, buttons or a touch-screen capable of receiving touch commands as well as displaying system information including a mode of operation as well as operating parameters. Injection shaft 104 generally attaches to the connector member 308.

Figure 2:
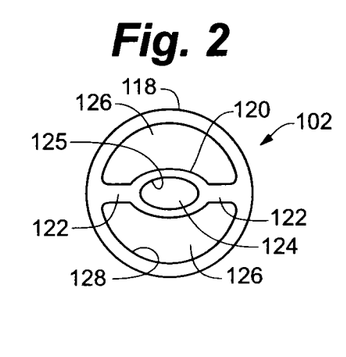
FIG. 2 is an end view of an embodiment of an adapter for maintaining the position of needleless fluid delivery system according to the present invention.
Figure 2A:
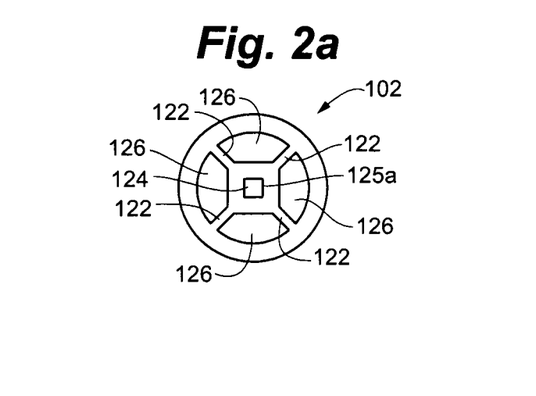
FIG. 2a is an end view of an embodiment of an adapter for maintaining the position of the needleless fluid delivery system according to the present invention.
Figure 2B:
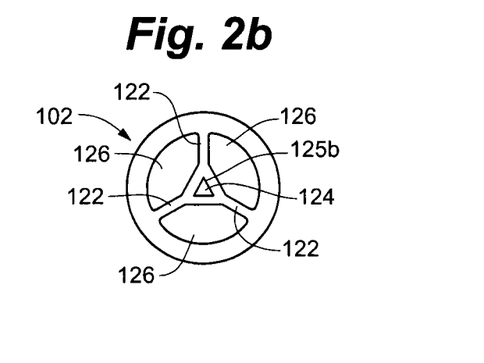
FIG. 2b is an end view of an embodiment of an adapter for maintaining the position of the needleless fluid delivery system according to the present invention.
Figure 3:
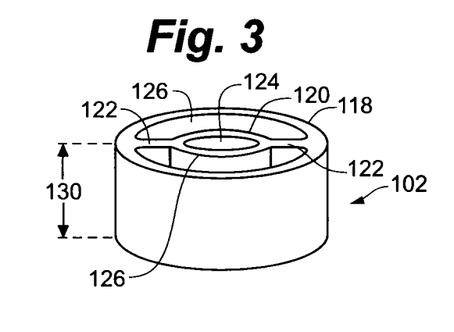
FIG. 3 is a perspective view of the adapter of maintaining the position of the needless fluid delivery system of FIG. 2.

As depicted in FIGS. 1, 2 and 3, the adapter ring 102 can be press fit within a working channel 116 of the cystoscope 100. The adapter ring 102 has an external shape 118 to match the cross section of the working channel 116. Furthermore, the adapter ring 102 includes an injection shaft ring 120 supported at least on opposing sides by spokes 122. The injection shaft ring 120 defines an interior channel 124 that matches the shape of the injection shaft 104. As illustrated, the interior channel 124 and injection shaft 104 each comprise a matched oval-shaped configuration 125 though it is to be understood that any non-round orientation can be utilized for interior channel 124 and injection shaft 104 such as, for example, a square configuration 125a as shown in FIG. 2a, a triangular configuration 125b as shown in FIG. 2b or other similar geometrical orientation such that turning and/or spinning of the injection shaft 104 within the interior channel 124 is prevented. The injection shaft ring 120 may be sized so as to not impede axial movement of the injection shaft 104. The adapter ring 102 further defines at least two additional fluid channels 126 for irrigation fluid or for alternate tool placement. The additional fluid channels 126 are defined by the area between the inner perimeter 128 of the adapter ring 102, the injection shaft ring 120 and spokes 122. The adapter ring 102 has an axial length 130 sufficient to extend within working channel 116 to prevent twisting of the adapter ring 102 during movement of the cystoscope 100 or the injection shaft 104.

Figure 4:
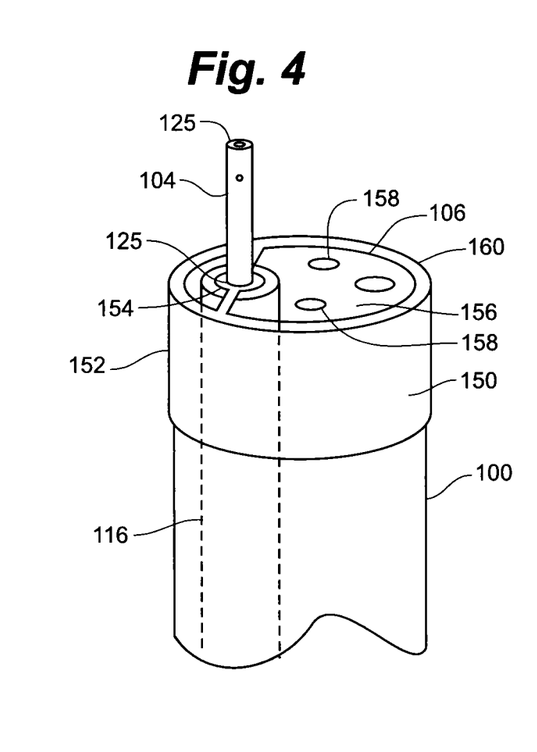
FIG. 4 is a perspective view of an embodiment of adapter ring sleeve disposed about the distal end of a cystoscope for delivering a therapeutic fluid to a treatment location with a needless fluid delivery system according to the present invention.
Figure 5:
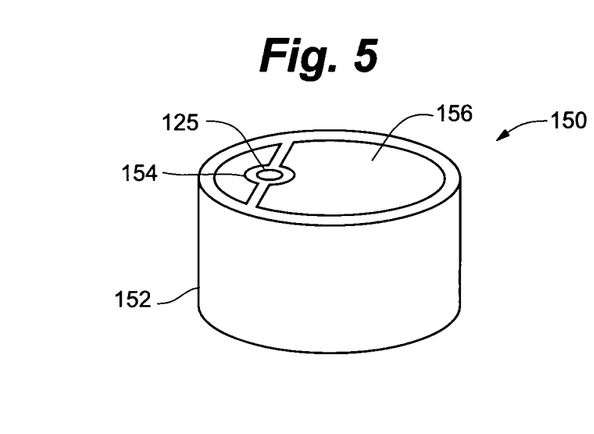
FIG. 5 is a perspective view of the adapter ring sleeve of FIG. 4.

In an alternate embodiment as depicted in FIGS. 4-5, an adapter ring 150 is disposed over the distal end 106 of the cystoscope 100. The injector shaft 103 extends distally from the working channel 116. Here, however, the adapter ring 150 comprises a sleeve body 152 that fits over the distal end 106 of cystoscope 101 with an injector shaft ring 154 disposed transverse to the injector shaft 104. The adapter ring 150 further defines an open channel 156 so as not to interfere with lighting fiber optics 158 and the viewing fiber optics 160.

While the present invention has been described in relation to treatment of the prostate, it should be understood that the invention may be used wherever appropriate and beneficial within an animal or human body, including but not limited to, urological applications, gynecological applications, urogynecological applications, renal applications, etc.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives.

The invention claimed is:

1. A method for fixing a needleless injection orifice relative to a flexible endoscope comprising:
    providing an endoscope having a flexible body between a proximal end and a distal end, the flexible body defining a work lumen and an optical viewing feature;
    attaching an adapter ring at the distal end of the flexible body, wherein the adapter ring includes a non-circular injector ring; and
    providing an injector tube having a cross-section corresponding to the non-circular injector ring, the injector tube including at least one injection orifice proximate an injection end of the injector tube; and
    advancing the injection end of the injector tube into the non-circular adapter ring, wherein rotation of the injector tube within the flexible body is prevented so as to fix an orientation of the at least one injection orifice.

2. The method of claim 1, wherein attaching the adapter ring at the distal end of the flexible body comprises press-fitting the adapter ring within a working lumen defined in the flexible body.

3. The method of claim 1, wherein attaching the adapter ring at the distal end of the flexible body comprises placing an adapter sleeve over the distal end of the flexible body.

4. A method for treating urinary tract tissue with a fluid comprising:
    providing an endoscope having a flexible body between a proximal end and a distal end, the flexible body defining a work lumen and an optical viewing feature;
    attaching an adapter ring at the distal end of the flexible body, wherein the adapter ring includes a non-circular injector ring; and
    providing an injector tube having a cross-section corresponding to the non-circular injector ring, the injector tube including at least one injection orifice proximate an injection end of the injector tube;
    selecting an administration orientation for the at least one injection orifice relative to the flexible body;
    advancing the injection end of the injector tube into the non-circular adapter ring such that the injection orifice corresponds to the administration orientation, wherein interaction of the cross-section of the injector tube and the non-circular adapter ring prevent rotation of the injector tube within the flexible body so as to fix the injection orifice in the administration orientation; and
    positioning the injection orifice proximate a treatment site.

5. The method of claim 4, wherein positioning the injection orifice proximate the treatment site comprises viewing the treatment site with the optical viewing feature.

6. The method of claim 4, wherein attaching the adapter ring at the distal end of the flexible body comprises press-fitting the adapter ring within a working lumen defined in the flexible body.

7. The method of claim 4, wherein attaching the adapter ring at the distal end of the flexible body comprises placing an adapter sleeve over the distal end of the flexible body.

8. The method of claim 4, further comprising:
    dispersing a pressurized treatment fluid at the treatment site.

9. A method for delivering a pressurized fluid to a treatment site, comprising:
    providing an endoscope having a work lumen and a non-circular adapter ring at a distal treatment end; and
    advancing an injector tube having an injection orifice through the work lumen wherein the injector tube has a cross-section corresponding to the non-circular adapter ring such that an administration orientation for the injection orifice is fixed relative to the work lumen.

10. The method of claim 9, further comprising:
positioning the injection orifice proximate a treatment site.

11. The method of claim 10, further comprising:
directing a pressurized treatment fluid through the injector tube.

12. The method of claim 11, further comprising:
administering the pressurized treatment fluid to the treatment site through the injection orifice.

13. The method of claim 9, further comprising:
viewing the position of the injection orifice relative to a treatment site with an optical feature in the endoscope.

14. The method of claim 9, further comprising:
attaching the injector tube to an injector device for pressurizing a treatment fluid.

15. The method of claim 9, wherein the step of providing the endoscope with the non-circular adapter ring at the distal treatment end, further comprises:
pressing the non-circular adapter ring into the work lumen.

16. The method of claim 9, wherein the step of providing the endoscope with the non-circular adapter ring at the distal treatment end, further comprises:
sliding a sleeve body over the distal treatment of the endoscope.

* * * * *